United States Patent
Shikinami

[19]

[11] Patent Number: 5,858,395
[45] Date of Patent: Jan. 12, 1999

[54] BASE POLYMER FOR TRANSDERMAL ABSORPTION PREPARATION COMPRISING A HEAT-SENSITIVE SEGMENTED POLYURETHANE

[75] Inventor: Yasuo Shikinami, Osaka, Japan

[73] Assignee: Takiron Co., Ltd., Osaka, Japan

[21] Appl. No.: 885,845

[22] Filed: Jun. 30, 1997

Related U.S. Application Data

[63] Continuation of Ser. No. 715,918, Sep. 19, 1996, abandoned, which is a continuation of Ser. No. 407,028, filed as PCT/JP94/01253 Jul. 29, 1994, published as WO95/04094 Feb. 9, 1995, abandoned.

[30] Foreign Application Priority Data

Jul. 30, 1993 [JP] Japan ................................ 5-208830

[51] Int. Cl.⁶ ................................................. A61F 13/00
[52] U.S. Cl. ........................... 424/449; 424/484; 424/486
[58] Field of Search ................................. 424/449, 484, 424/486

[56] References Cited

FOREIGN PATENT DOCUMENTS

| | | |
|---|---|---|
| 0043974 | 1/1982 | European Pat. Off. . |
| 0299758 | 1/1989 | European Pat. Off. . |
| 93/09796 | 5/1993 | WIPO ............................ A61K 9/70 |

*Primary Examiner*—D. Gabrielle Brouillette
*Attorney, Agent, or Firm*—Sughrue, Mion, Zinn, Macpeak & Seas, PLLC

[57] ABSTRACT

A base polymer for transdermal absorption preparation, which is a solid at ordinary temperatures, which becomes a liquid having a low viscosity near the skin temperature of human, which has heat-sensitive and water-sensitive properties as it has a hydrophilic segment, which is capable of stably storing the drug which conventionally has not been easily formulated into a transdermal absorption preparation, and which is capable of effecting transdermal absorption of the drug at a high releasing ratio and yet in a slow-releasing manner with less skin irritation. The base polymer comprises a heat-sensitive segment polyurethane which is represented by the following general formula:

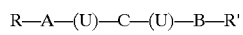

wherein A and B each represents a polymer of ethylene oxide, propylene oxide, tetramethylene oxide or 1,2-butylene oxide, or a random or block copolymer thereof, R and R' each represents a terminal H, $CH_3$, $C_2H_5$, $C_3H_7$ or $C_4H_9$ thereof, and A=B or A≠B, R=R' or R≠R', C represents a constituting structure which is a moiety of a diisocyanate compound excluding two diisocyanate groups, (U) represents a urethane bond, and at least one of A and B is hydrophilic and at the same time at least one of A and B is characterized in that it melts near the temperature of the human skin.

7 Claims, 1 Drawing Sheet

BASE POLYMER FOR TRANSDERMAL ABSORPTION PREPARATION COMPRISING A HEAT-SENSITIVE SEGMENTED POLYURETHANE

This is a Continuation of application Ser. No. 08/715,918 filed Sep. 19, 1996, now abandoned; which in turn is a Continuation of application Ser. No. 08/407,028, filed as PCT/JP94/01253 Jul. 29, 1994, published as WO95/04094 Feb. 9, 1995, (now abandoned).

TECHNICAL FIELD

This invention relates to a polymer which is used as a base for the purpose of storing and releasing a drug in a transdermal absorption preparation which is a system for slowly releasing the drug into the body through the skin (TTS: Transdermal Therapeutic System).

TECHNICAL BACKGROUND

The transdermal absorption preparations which are now put into a practical use or under development can be roughly classified from the standpoint of storage and release of drugs into (1) a reservoir type, (2) a matrix type, (3) a pressure-sensitive adhesive (autohesion) tape, (4) a multilayer adhesive tape, and (5) others. Each of the drug-storing layers uses, as a base thereof, a silicone oil in (1), a hydrophilic polymer such as polyvinylalcohol (PVA), polyvinylpyrrolidone (PVP), etc., or a silicone elastomer in (2), and an acrylate type adhesive (PSA) in (3). The above-described (4) includes a preparation in which adhesive layers having different affinities to the drug are overlaid in a multilayer so as to control a releasing property. In addition, various polymers such as a natural rubber, synthetic rubbers, celluloses, synthetic resins, etc. are investigated, but they are presently not put into a practical use.

The purpose of ordinary transdermal absorption preparations is to naturally diffuse the drug in the base and to distribute and transfer the drug to the skin side and allow the drug to be absorbed by the living body upon merely adhering the preparation to the skin surface by utilizing the concentration gradient of the drug as a driving power for the diffusion and release without depending upon a method of applying an external energy such as electricity or ultrasonic wave. Thus, the use of the ordinary transdermal absorption preparation is convenient. In order to achieve the above purpose, it is necessary that the base has at least the following chemical and morphological characteristics.

(a) The base and the drug are required to have an appropriate affinity (compatibility). The term "appropriate" used herein means that the affinity is such a degree that the drug is capable of leaving the base and transferring to the skin. The releasing ratio of the drug varies remarkably depending upon the above affinity, and also the 0 order release is obtainable.

(b) The base is required to be a liquid at ordinary temperatures or, apparently, to be in an intermediate form between solid and liquid states such as a swollen gel which is a liquid-containing form, so that the drug (in particular, a solid drug) can diffuse in the base. In the reservoir type practically used, a silicone oil which is a liquid is used, and in the matrix type, a hydrogel of a water-soluble polymer is used. Also, when a silicone elastomer which is a rubbery polymer is used, the drug is dispersed therein together with a solvent. In the case of an adhesive tape, a tackifier is dispersed as a liquid in an adhesive, and the adhesive per se is a gel which is in an intermediate region between solid and liquid forms. These facts satisfy the above-described requirements of the base.

However, the type wherein the drug is supported in the adhesive does not generally have a relatively high releasing ratio of the drug. Also, although an oily or aqueous swollen gel has the releasing ratio slightly higher than that of the above type, some drugs may have problems in the storage stability when a preparation is produced by using the swollen gel. More specifically, there are possibility of changes in the initial dose of the drug due to release of a solvent or water as a swelling medium with the passage of time, as well as the modification of the drug by a reaction with a dispersing medium. Further, in the case of the reservoir type wherein a liquid drug is blended in a liquid with a powdery material such as an emulsifying base, or wherein a solid drug is dispersed together with a liquid co-solvent, these components tend to transfer to the surface of the preparation during storage and hence it is unavoidable that the drug accumulates at a high concentration in the release-controlling membrane, and there may be a problem that the drug is drastically released at the initial stage of the application.

(c) The base is required to have a low irritation to the skin or substantially no irritation. Since the plaster is generally replaced repeatedly, a skin inflammation causes a great problem. Thus, reduction in the size of the preparation is advantageous.

(d) Even if the drug takes effect with only a small dose of several micrograms and is unstable such that the drug is easily modified by air, moisture, heat, or the like, it is necessary that the drug can be stored stably and released at a high releasing ratio. The drug of which formulation into a transdermal absorption preparation is particularly significant is those having a high decomposition ratio in the digestive tract, liver, etc., a short half-life and a low effective serum concentration. Most of these drugs have the above-described characteristics and hence it is necessary to take any countermeasure thereto.

(e) Even if the drug is water-soluble and has poor permeability and absorption through the skin, it is necessary that the drug can be slowly released into the body at a high efficiency. It is desirable that the above can be achieved, in particular, without using an absorption enhancer, etc. Recently, studies on the absorption enhancer have been made extensively, but troublesome issues are involved therein such as the necessity of investigation on the toxicity of the enhancer itself.

For solving the above-described problems, the present inventors developed the base polymers described in JP-A-63-108019 and JP-A-63-146812 (The term "JP-A" as used herein means an unexamined published Japanese patent application.). That is, the base polymer is a heat-sensitive and water-sensitive amphipathic polymer which is a segment polyurethane in which block linkages are adjusted in such a manner that the hydrophilicity increases as the block comes close to one end of the polymer molecule and the hydrophobicity or lipophilicity increases as the block comes close to other end of the polymer molecule.

In the above amphipathic polymer compound, a balance of hydrophilicity and the hydrophobicity and a molecular weight of constituting molecules of the segments are adjusted so that the polymer can dissolve or melt in response to water or heat. When it is dissolved or molten, the hydrophilic segment solubilizes a hydrophilic drug and the hydrophobic (lipophilic) segment solubilizes a hydrophobic (lipophilic) drug. Generally, drugs have a structure containing polar groups or non-polar groups and have hydrophilic, lipophilic or amphipathic characteristics and is dissolved in the same type of solvents. Even if the drug is exceptionally insoluble in solvents, the drug takes effect as long as it is dissolved in a very minute amount and, therefore, the drug may be investigated at a level of a very low solubility. Accordingly, the drug is necessarily assigned to any of the above-described hydrophilic, lipophilic and amphipathic groupings. Also, since the solubilization by this polymer makes it possible to dissolve the drug at a molecular level, i.e., as a molecular dispersion, it is particularly effective for slow-releasing of a physiologically active material which takes effect with a very minute dose of several micrograms per prescription. In other word, in order to store a drug which has a low effective serum concentration and which takes effect with a very minute dose and to release the drug, dispersion of the drug at a molecular level is essential. Most of these physiologically active materials are also easily decomposed by oxygen, water, heat, etc. However, as the term "heat-sensitive property" connotes, the polymer keeps a solid state at ordinary temperatures below 30° C. and hence the drug can be stably maintained in a solid. When applied to the surface of a living body, the polymer is easily transformed from a solid to a liquid by sharply responding to the temperature of the body surface. Also, the polymer is dissolved by a small amount of water exuded from the body surface, and the drug is diffused and transferred in the polymer. Although some drugs are in a liquid state at ordinary temperatures, most of drugs are in a solid state. In order to release a solid drug by diffusion in a base and to absorb the drug into the skin, the base must be either a liquid or a gel material. The above-mentioned polymer satisfies this requirement and can be used as a base polymer for a transdermal absorption preparation applicable to many drugs.

However, as a result of further studies, the present inventors found that a heat-sensitive polymer having a higher hydrophilicity is required for, among others, hydrophilic drugs which are difficult to be absorbed by and permeate into the skin. Also, it has been found that, in order to release these drugs efficiently within a short period of time, for example, a predetermined time of from 24 to 48 hours, the dissolved and molten polymer is required to have a lower viscosity and form an environment in which the drug is easily diffused. The present invention was completed in the light of such a demand.

DISCLOSURE OF THE INVENTION

As a result of extensive studies, the present inventors found that the above demand can be satisfied by the base polymer for the transdermal absorption preparation of the present invention which comprises an amphipathic segment polyurethane represented by the general formula:

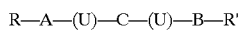

wherein A and B each represents a polymer of ethylene oxide (EO), propylene oxide (PO), tetramethylene oxide (TMO) or 1,2-butylene oxide (BO), or a random or block copolymer thereof, R and R' each represents a terminal H, $CH_3$, $C_2H_5$, $C_3H_7$ or $C_4H_9$, A=B or A≠B, R=R' or R≠R', C represents a constituting structure which is a moiety of a diisocyanate compound excluding two diisocyanate groups, and (U) represents a urethane bond, and at least one of A and B is hydrophilic and at the same time least one of A and B has a characteristic such that it melts near the temperature of human skin.

The constituting structure of the diisocyanate compound as referred to in the present invention means a moiety of the diisocyanate compound hereinafter described, excluding two isocyanate groups (—NCO).

The temperature of human skin as referred to in the present invention means a temperature range of from 30° to 37° C., and a temperature near the human skin temperature means a temperature range of from 30° to 40° C.

The hydrophilicity in A and B as referred to in the present invention means a characteristic showing an affinity to water, and a compound containing a polar group or a dissociable group such as —OH (a hydroxy group), —COOH (a carboxyl group), —$NH_2$ (an amino group), >CO (a carbonyl group), —$SO_3H$ (a sulfo group), —O— (an ether), or the like, which is an atomic group forming a weak bond to a water molecule by an electrostatic interaction or a hydrogen bond shows such a property. From the standpoint of biocompatibility, a compound containing —OH or —O— is that having a preferred hydrophilic property.

Illustrative examples of the structure of the general formula:

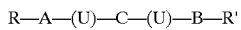

are shown in Table 1 below.

TABLE 1

① $R(-OCH_2CH_2-)_l(-U-)-C(-U-)(-CH_2CH_2O-)_{l'}R'$  l = l' or l ≠ l'

② $R(-OCH_2CH_2-)_l(-U-)-C(-U-)(-CH_2\overset{CH_3}{\underset{|}{C}}HO-)_m R'$

③ $R(-OCH_2CH_2-)_l(-U-)-C(-U-)(-CH_2CH_2CH_2CH_2O-)_n R'$

④ $R(-OCH_2CH_2-)_l(-U-)-C(-U-)(-CH_2\overset{C_2H_5}{\underset{|}{C}}HO-)_p R'$ ⑤ $R(-EO-)_l(-U-)-C(-U-)(-EO/PO-)_q R'$ ⑥ $R(-EO/PO-)_q(-U-)-C(-U-)(-EO/PO-)_{q'} R'$  q = q' or q ≠ q'

⑦ $R(-EO/PO-)_q(-U-)-C(-U-)(-PO-)_m R'$

⑧ $R(-EO/PO-)_q(-U-)-C(-U-)(-TMO-)_r R'$

⑨ $R(-EO/PO-)_q(-U-)-C(-U-)(-BO-)_p R'$

⑩ $R(-EO-)_l(-U-)-C(-U-)(-EO/TMO-)_s R'$

⑪ $R(-EO-)_l(-U-)-C(-U-)(-EO/BO-)_t R'$

⑫ $R(-EO/PO-)_q(-U-)-C(-U-)(-EO/TMO-)_s R'$

⑬ $R(-EO/PO-)_q(-U-)-C(-U-)(-EO/BO-)_t R'$ wherein EO is —OCH$_2$CH$_2$—, PO is

TMO is —CH$_2$CH$_2$CH$_2$CH$_2$O—, BO is

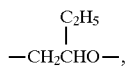

EO/PO, EO/TMO and EO/BO each represents a block or random copolymer thereof, —(U)— represents a urethane bond, C represents a structure of a moiety of a diisocyanate compound excluding two isocyanate groups (—NCO), l, l', m, n, p, q, q', r, s and t each represents a positive integer, and R and R' each represents H, CH$_3$, C$_2$H$_5$, C$_3$H$_7$ or C$_4$H$_9$.

In this case, the necessity of at least one of A and B being hydrophilic is for the purpose of dissolving the hydrophilic drug in a relatively large amount, while the amount is a low concentration level at a degree of taking effect. The hydrophilic drug refers to the opposite of the lipophilic drug, and shows an affinity to water. Basically, the hydrophilic drug has a certain degree of solubility in water, and examples of the drug used together with the polymer of the present invention include prostaglandins, nitroglycerin, atropine, strophanthin, isoproterenol hydrochloride, oxprenolol hydrochloride and captopril, etc.

Also, this segment provides a moisture (water) absorbability and is a basis for a water-sensitivity by which the polymer is easily dissolved in a very minute amount of water on the body surface. The water-sensitivity refers to a property of a sharp sensitivity to water in such a manner that the polymer itself has a moisture absorbability, dissolves upon absorption of a small amount of water (moisture), transforms from a solid to a liquid containing water by further absorbing water by itself, and, at the same time, a melting temperature thereof reduces.

The basis for the hydrophilicity is an ether oxygen (—O—) in the molecular chain and —OH at a terminus of the molecular chain. Since —CH$_3$ and —C$_2$H$_5$ side chains attached to the methylene chain (—CH$_2$—) prevent an access of water to the ether oxygen, ethylene oxide which has no such side chain and which has a proportion that one ether oxygen exists per two methylene groups is, among others, most hydrophilic. Polymers having side chains are more hydrophobic, and the hydrophobicity increases, as the size of an alkyl side chain increases. Further, the terminal —OH shows hydrophilicity but, when an alkoxy terminus such as —OCH$_3$, —OC$_2$H$_5$, —OC$_3$H$_7$ or —OC$_4$H$_9$ is formed, the hydrophobicity increases depending on the order of size of the alkyl moiety shown herein. Accordingly, when the segments in both sides of the urethane bond are EO, the degree of hydrophilicity can be delicately adjusted by making the termini hydrophobic using the alkoxy termini.

In order to take advantage of the inherent property of the segment, an excessively long alkyl chain length in the alkoxy termini is not preferred since it affects the hydrophilicity of the whole molecule and also alters a melting temperature of the polymer. As one approach, the terminus can be a long alkyl chain or an ester bond with an aromatic carboxylic acid as in the conventionally used non-ionic surface active agents. However, in this case, due to an cohesive force of the ester bond, an interaction of the drug with the ester bond is involved in addition to the interaction between the ether bond in the segment and the drug and hence the control of slow-releasing becomes difficult. Also, similar to the case where the terminus is the alkoxy terminus of a long alkyl chain, the ester bond is considered to affect greatly the solidifying point and the amphipathicity, the alkoxy terminus with a short alkyl chain within the scope of the present invention is preferred.

Further, the degree of hydrophilicity (hydrophobicity) can be adjusted by segmenting the above-described copolymer containing EO in proportion to a ratio of EO. From this viewpoint, a combination of segments on both sides of the diisocyanate compound can be illustrated as shown in Table 1.

The heat-sensitivity which causes transformation from a solid at ordinary temperature to a viscous liquid upon melting near the surface temperature of the human skin can be adjusted by a molecular weight of EO or tetramethylene oxide (TMO). However, when the viscosity in a molten state is considered, the heat-sensitivity is preferably adjusted by EO. Other alkylene oxides are liquid at ordinary temperatures and are not factors of the heat-sensitivity. Rather, the other alkylene oxides are expected to have a function as a hydrophobicity-providing segment of the amphipathicity and serves as a factor of an affinity to a hydrophobic drug. In the case of the copolymer containing EO, copolymers which satisfy the requirement for transformation by heat exist, depending upon a ratio and a molecular weight of EO, and a type of the copolymer (whether block or random) and a molecular weight of EO contained therein, but many of the copolymers have no definite solidifying and melting temperatures as compared with those of the polymer of EO alone. Also, these copolymers are not a crystalline hard solid and thus there is a problem in the use of such copolymers as a stable solid phase for storing the drug for a long period of time. Further, since such copolymers necessarily have relatively high molecular weights due to the necessity in the chemical structure thereof, the viscosity in the molten state is relatively high. Such a high viscosity is not preferred from the standpoint of diffusion of the drug, but the copolymers can be used depending upon the type of the drug (for example, more hydrophobic drugs). The term "ordinary temperatures" as used in the present invention means a temperature range which is not lower than 0° C. and lower than 30° C.

An example having a polymer of EO alone in at least one of the segments is described hereinafter. In the polyethylene glycols which are polymers of EO alone, an average molecular weight of the polymer which undergoes a solid-liquid transformation near the temperature of skin surface, at 30° to 40° C., is about 800 to 1200 and, for example, a solidifying temperature of the polyethylene glycol having an average molecular weight of 1000 is 37.1° C. (the regulated value in *Pharmacopeia of Japan:* 35° to 39° C.), and thus that having an average molecular weight of from 800 to 1200 is preferably selected. The term "average molecular weight" as used in the present specification is a number average molecular weight, unless otherwise indicated.

In the case of (1) in Table 1, when an average molecular weight of 1000 is used in either of EO segments, an average molecular weight of 200 to 1000 may be used in the other segment. At least one of the termini can be an alkyl ether, and at least one of the termini can be —OH as it is. The polymer in which the both termini are —OH may be used, but it may cause problems with respect to the releasing ratio and the releasing pattern since it has excessive affinity to the hydrophilic drug. An attention should be paid to a solidifying point, for example, when segments of a molecular weight of 1000 having a solidifying point of 37.1° C. are used in both segments. The solidifying point of the polymer having an average molecular weight of 2000 in the case where polyethylene glycols having an average molecular weight of 1000 are merely bonded is about 45° C., but the solidifying point in the above-described case is substantially the same as the solidifying point of the polymer having an average molecular weight of 1000. The solidifying point reduces by a degree of only about 1° to 2° C. depending upon the terminal alkyl group. This indicates that the urethane bond between the linked segments avoid the affects on the solidifying point caused by the EO chains in the polyethylene glycol, the length of the molecule and the intermolecular or intramolecular cohesive force produced by the terminal groups, whereby the intermolecular or intramolecular motion inherent to the segment are made independent and thus the solidifying point based on an average molecular weight of 1000 appears substantially as it is. The above facts are the basis for designing the polymer molecule satisfying the object of the present invention. That is, even when the total molecular weight becomes large, the solidifying point thereof remains at a temperature near that of the constituting segments and thus it is possible that one of the segments is provided with others functions.

The construction of (2) in Table 1 is an example in which a propylene oxide (PO) chain is introduced in one of the segments, and the PO chain is relatively hydrophobic due to —$CH_3$ present in the side chain. However, if the molecular weight is several hundreds or below and the terminal —OH remains, a hydrophilic characteristic still remains due to the effect of this hydroxy group. Accordingly, in the case of (2) in which the EO segment is present in one side, a number average molecular weight of the PO segment of up to about 1000, preferably from about 300 to about 1000, is used. This is also a limitation of the length with consideration of the melt viscosity.

The construction (3) and (4) in Table 1 are examples having more hydrophobic segments in one side and are useful for a hydrophobic drug. The molecular weight of these segments is suitably up to a number average molecular weight of about 1500, preferably from about 300 to about 1500, with consideration of the same factor as in (2).

The construction (5) in Table 1 is the case using an EO/PO copolymer in one side. Although a degree of hydrophilicity and hydrophobicity varies depending upon the ratio and the molecular weight of the EO and the type of copolymer, the polymer can be adjusted to be more hydrophobic than the case in which the both segments are EO polymers and can be adjusted to be more hydrophilic than the case of (2). Also, its melt viscosity is between the cases of (1) and (2). Copolymers are commonly inferior in the crystallinity to a homopolymer. Accordingly, when a crystalline segment of the EO polymer is used in one side, the heat-sensitivity thereof varies sharply. Also, in the case of a random copolymer, the molecular motion of the molecular units randomly arranged in the random copolymer, particularly an actively moving characteristic of the small units therein, provides desirable results to the diffusion and the release of the drug, etc.

Further, a copolymer ratio of EO and other alkylene oxides in the case of (5) and the subsequent polymers is appropriately selected in the range of 10 to 90%, preferably 30 to 70%, of EO at a molar ratio.

The above-described facts are similarly applied to the combination of (6) and the subsequent polymers in Table 1 and, with consideration of characteristics of drugs and releasing patterns required for drugs, a combination of these segments can be selected. Also, the type of the terminal groups can be selected in a similar manner.

The total molecular weight of the polymers represented by these structural formulae varies depending upon the combination of each of the segments, but is approximately from 1000 to 6000, preferably from 1200 to 2500.

The diisocyanate having the structure of the intervening C in the above-described general formula can be selected from p-phenylene diisocyanate, 2,4-toluylene diisocyanate (TDI), 4,4-diphenylmethane diisocyanate (MDI), naphthalene 1,5-diisocyanate, hexamethylene diisocyanate, tetramethylene diisocyanate, lysine diisocyanate, xylylene diisocyanate and hydrogenated TDI, hydrogenated MDI, dicyclohexyldimethylmethane p,p'-diisocyanate, isophorone diisocyanate, etc. However, since a structure in which the both segments are extending linearly tends to exhibit a heat-sensitivity more sharply and to have a low melt viscosity, a diisocyanate having a linear structure is desirable and also an aliphatic diisocyanate is more preferred than an aromatic or alicyclic diisocyanate in view of ease in molecular motion. A polyfunctional compound such as a triisocyanate may be used, but is not preferred since the melt viscosity thereof is generally high.

The cohesive force of the urethane bond (—NH—CO—O—) formed by the reaction between such a diisocyanate and an alkylene glycol is 8.74 (kcal/mol). Since this value is high as compared with 0.68 for —$CH_2$—, 1.36 for —CH($CH_3$)—, 1.77 for —$CH_3$ and 1.00 for —O— which are constituting unit molecules of alkylene glycols and functions to increase the melt viscosity, it is convenient for adjusting a viscosity to a preferable degree for a drug storing layer. In fact, the polymer according to the present invention having these intervening urethane bonds has a melt viscosity slightly higher than that of an alkylene glycol having the same molecular weight and, therefore, is effective for delicately controlling the drug releasing. If the melt viscosity is too low, it is not preferred since the polymer flows down from the skin. The urethane bonds have an appropriate molecular length suitable as a spacer between the both segments and have a suitable function for an independent molecular motion of each segment.

A method for producing the polymer of the present invention is described hereinafter.

A method for producing the polymer of the present invention comprises reacting an alkylene glycol having segments corresponding to A and B of the general formula:

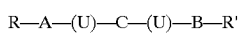

with a diisocyanate having a constituting structure of C.

In the above reaction, the alkylene glycol having A and B segments is preferably dehydrated and dried previously using a vacuum dryer, etc. The drying temperature in this case is preferably from 50° to 80° C.

In reacting each of A, B and C components, the reaction is preferably conducted in an $N_2$ gas atmosphere at 50° to 80° C.

The alkylene glycol having the A and B segments used in the reaction has terminal hydroxy groups, and can be prepared by a conventionally known process. Alternatively, a commercially available compound may be used.

The diisocyanate which is reacted with the alkylene glycol having A and B segments include the above-described compounds. Diisocyanates prepared by a conventionally known method can be used, or commercially available compounds can be used.

Other methods for producing the polymers of the present invention include a method using a monoalkoxyalkylene glycol having an alkoxy group at one of A or B or the both and reacting this alkylene glycol with a diisocyanate having a constituting structure of C in the same manner as described above.

A method for incorporating a drug into the polymer of the present invention comprises mixing a drug with a polymer which has been molten by warming at 40° to 60° C., and dispersing and dissolving the drug.

Action

The base polymer for the transdermal absorption preparation of the present invention designed based on the above-described intention of the molecular design has the following action and effect.

(1) The base polymer of the present invention is crystalline or paste-like solid at ordinary temperature below 30° C., and is capable of stably storing a physiologically active agent which is easily deteriorated by air, moisture or heat (e.g., an abortion-inducing agent, a hypnotic, a sedative, a tranquilizer, an anticonvulsant, a muscle relaxant, an anti-parkinsonian agent, an analgesic, an antipyretic, an anti-inflammatory agent, a local anesthetic, an anti-ulcer agent, a microcidal agent, a hormone, an androgen steroid, estrogen, a sympathetic agent, a cardiovascular agent, a diuretic agent, carcinostatic and anticancer agents, an anti-hypoglycemic agent and nutrients), and, in particular, the drug which is solid at ordinary temperatures does not undergo transfer during the storage.

(2) Since the base polymer easily becomes a liquid having a low viscosity at a temperature near the skin temperature of the living body, which is an amphipathic liquid in which both the water-soluble and hydrophilic segment and the hydrophobic segment exist together, it dissolves most of the drugs which are solid at ordinary temperatures if its amounts is a relatively small amount but can take effect and uniformly disperses the drug in a molecular state at the portion of the segment having a high affinity to the drug. Accordingly, in most of the cases, a solvent is not necessary for dissolving the drug in the polymer, and thus a means for completely evaporating the solvent is not required and a possible risk caused by the toxicity of the residual solvent can be avoided.

(3) The viscosity of the molten base polymer is 2,000 centipoise or less which is a low value as compared with the viscosity of approximately 5,000 to 10,000 centipoise of the polymers described in the above JP-A-63-108019 and JP-A-63-146812. The viscosity referred to herein means a viscosity measured by Brookfield type rotational viscometer using No. 4 rotor at a rotation of 60 r.p.m. Accordingly, the drug dissolved in the base polymer diffuses therein and is transferred to the skin side at a high proportion. In particular, in the system wherein a phase-separated membrane comprising the same polymer as the base polymer as a buried microphase is closely contacted with the layer of the base polymer, the polymer becomes a liquid at a temperature near the skin temperature and is fluidized and transferred to the skin from the membrane, and thus the efficiency of the drug to reach to the skin is improved. Such a system is effective for producing a transdermal absorption preparation having a high releasing ratio in which a drug is contained at a low concentration or a physiologically active substance is contained in a very minute amount of from several micrograms to several hundreds micrograms per prescription.

According to T. Higuchi (*J. Soc. Cosmetic Chemists,* 11, 85 (1960)), the releasing amount of the drug with respect to the release from a solution state has the following correlation at the initial stage:

$$M = 2Co\left(\frac{Dvt}{\pi}\right)^{1/2}$$

wherein:
M: Amount of drug released per unit area
Co: Initial concentration of drug in base
Dv: Diffusion coefficient of drug in base
t: Time, if the releasing stage from the base material is a rate-determining step. That is, the releasing amount is proportional to the initial concentration, the diffusion coefficient and the time. When Co and t are constant, the releasing ratio depends on the diffusion coefficient. Thus, it would be understood that there is significance in the present invention where the viscosity is reduced for the purpose of increasing the diffusion coefficient.

Incidentally, according to the formula of Wilke (Wilke: *Chem. Eng. Progr.,* 45, 218 (1949), the diffusion coefficient in the liquid phase is indicated as follows:

$$D_L = 7.4 \times 10^{-8} \frac{(xM_2)^{1/2}T}{\mu_2 V_1^{0.6}}$$

wherein:
$D_L$: Diffusion coefficient (cm²/sec) of solute molecule at temperature T (°K.) in a dilute solution comprising solvent 2 and solute 1
$M_2, \mu_2$: Molecular weight and viscosity (centipoise) of solvent
x: Degree of association of solvent
$V_1$: Molar volume at boiling point of solute Accordingly, it is understood from the above formula that the diffusion coefficient increases as the viscosity of solvent decreases. That is, it is well supported that as the viscosity of the base after melting decreases, the diffusion coefficient of the drug increases whereby the transfer to the skin side which is a low concentration side increases.

(4) Since an EO polymer is selected as a hydrophilic segment, its crystal is liquefied at once in response to heat. Also, the crystal is easily dissolved in water exuded from the living body, and the sensitivity to water is sharp. Further, the base easily dissolves a hydrophilic drug. However, since the polymer can be made amphipathic by using a hydrophobic segment as the other segment or using an alkoxy groups of an alkyl chain as the terminal groups, the degree of the affinity to a hydrophilic drug can be controlled, and the releasing ratio of a hydrophilic drug which is difficult to be absorbed by or permeate through the skin can be improved.

(5) In the case of a transdermal absorption preparation having a structure in which the base polymer of the present invention is molten and reached to and contacted with the surface of the skin, a less absorbable drug can be absorbed through the skin at a relatively effective way, since the base polymer can be made amphipathic and thereby exhibits good affinity to the lipids of the skin. Thus, it is not necessary to use an additional absorption enhancer.

(6) The base polymer of the present invention has a molecular structure similar to a polyalkylene glycol which has been conventionally used as an additive to drugs and cosmetics. For this reason, skin irritation and toxicity are substantially not observed, and the polymer is safe. Also, the polymer is safe since residual monomers as in acrylic polymers do not exist.

(7) Although the viscosity of the polymer in a molten state is low to show advantage for diffusion, but is not so low that the polymer flows down from the skin upon application. The degree of the viscosity is that required for suitably spreading the base on the skin surface which is advantageous for absorption of the drug from the skin. The adjustment of such a melt viscosity has been achieved by adjusting the type and the molecular weight of the segments and the total molecular weight of the base polymer.

BEST MODE FOR CARRYING OUT THE INVENTION

Figure 1:
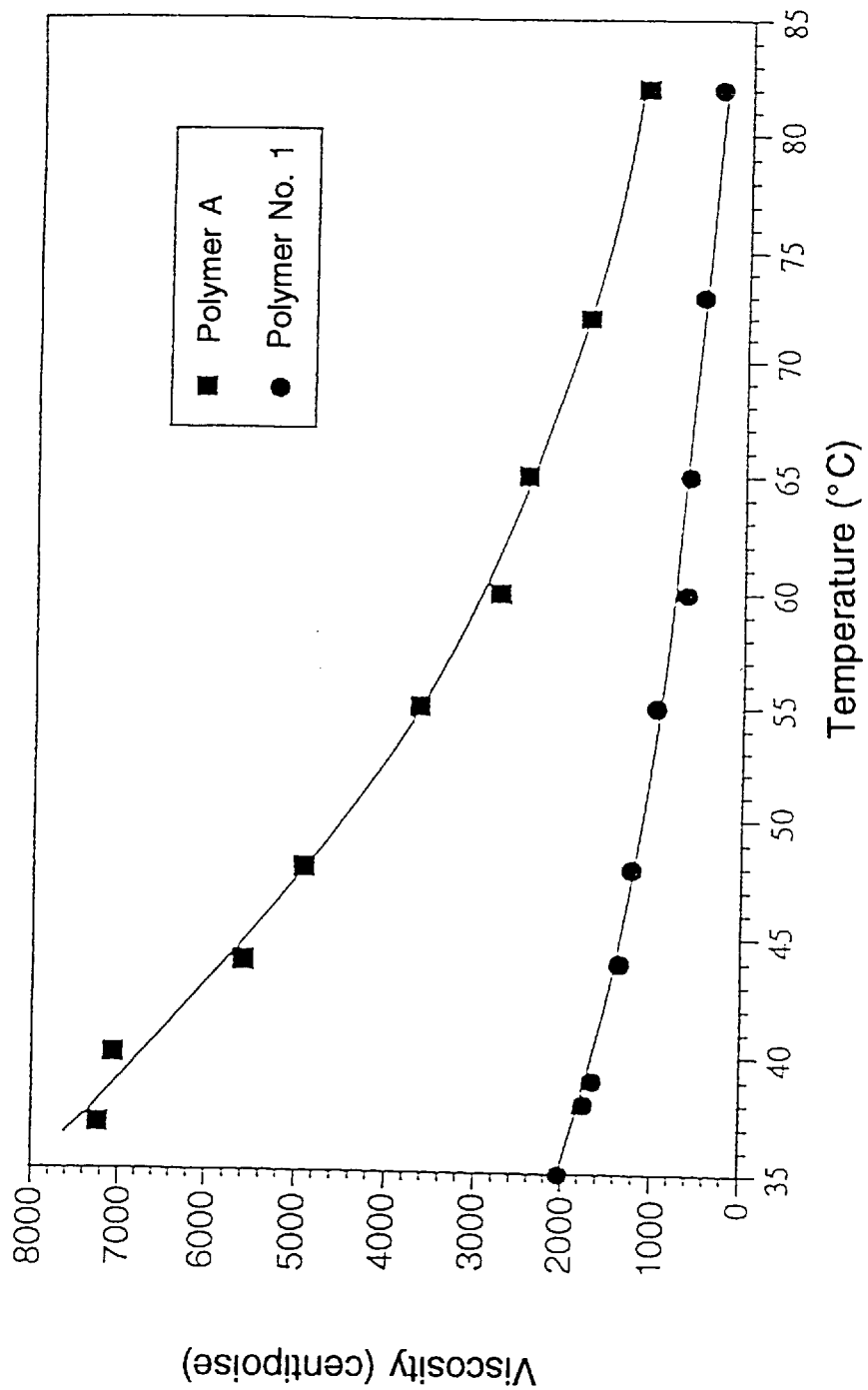
FIG. 1 is a graph showing a relationship between the melt viscosity and the temperature with respect to No. 1 of base polymer in Example 1 of the present invention and the polymer described in Example 2 of JP-A-63-146812.

Examples of the present invention are hereinafter described.

TABLE 2

| No. | Structure | Solidifying Point (°C.) |
|---|---|---|
| (1) | H-R(400)-(U)-C-(U)-PEO(1000)-H | 34.9–35.6 |
| (2) | H-R(400)-(U)-C-(U)-PEO(1000)-CH$_3$ | 35.7–37.5 |
| (3) | H-PPO(400)-(U)-C-(U)-PEO(1000)-H | 35.6–36.6 |
| (4) | H-PEO(400)-(U)-C-(U)-PEO(1000)-C$_2$H$_5$ | 36.2–37.4 |
| (5) | H$_3$C-PEO(400)-(U)-C'-(U)-PEO(1000)-H | 36.1–37.2 |
| (6) | H$_3$C-PEO(400)-(U)-C'-(U)-PEO(1000)-CH$_3$ | 36.1–37.9 |

In Table 2, the numerals in () denotes a number average molecular weight, PEO represents polyethylene oxide, PPO represents polypropylene oxide, R represents a random copolymer having EO/PO=1/1 molar ratio, C represents —(CH$_2$)$_6$— which is a structure of hexamethylene diisocyanate, C' represents —CH$_2$—C$_6$H$_4$—CH$_2$— which is a structure of xylylene diisocyanate, and —(U)— represents a urethane bond.

All of the six types of polymers for a base shown in Table 2 were synthesized by the following synthesis method, and the solidifying point of the resulting polymer was measured by the differential scanning type calorimeter (DSC-220C, produced by Seiko Denshi Kogyo).

(Synthesis Method)

To describe the synthesis method by taking, for instance, Polymer No. 1 as an example, a commercially available R (400) and PEG (1000) were well dehydrated and dried at 60° C. under reduced pressure using a vacuum dryer. The OH value of these alkylene glycols and the OH value and the NCO value of hexamethylene diisocyanate (HMDI) were measured.

The measurement of the OH value was conducted according to the method stipulated in Fats and Oils Test Method of *Pharmacopeia of Japan,* and the measurement of the NCO value was conducted according to the following method.

A 30 ml portion of a toluene solution of 0.5 mol di-n-butylamine was placed in an Erlenmeyer flask, and an accurately weighed sample was dissolved therein. Thereafter, 100 ml of 2-propenol and several drops of bromophenol blue as an indicator were added thereto, and the mixture was titrated with a 0.5N hydrochloric acid standard solution. The procedure was repeated for two samples, and the NCO value was calculated by the following formula:

$$NCO \text{ Value} = \frac{42.02 \times 0.5 \times (B - A) \times F \times 100}{1000 \times S}$$

A: Amount (ml) of hydrochloric acid standard solution required for the actual test B: Amount (ml) of hydrochloric acid standard solution required for the blank test F: Potency of 0.5N hydrochloric acid standard solution S: Weight (g) of the sample presented to the test After measuring the OH value of alkylene glycol and the OH value and the NCO value of hexamethylene diisocyanate (HMDI), they were mixed at a molar ratio of R(400):PEG (1000):HMDI =1:1:1 and reacted in an N$_2$ gas atmosphere at 70° C. using a small amount of di-n-butyltin dilaurate as a catalyst. In this case, the reaction was conducted while adding dropwise HMDI to the polyols. The end point of the reaction was assumed by IR absorption spectrum when an absorption at 2250 cm$^{-1}$ by the isocyanate group disappeared.

(Comparison of Melt Viscosity)

The temperature of the polymer described in Example 2 of JP-A-63-146812 represented by the following structural formula (hereinafter referred to as Polymer A) and Polymer No. 1 of the present invention was elevated higher than the melting points, and their viscosities were measured for comparison using a B type viscometer (Rotor No. 4, at 60 r.p.m.). The results obtained are shown in FIG. 1.

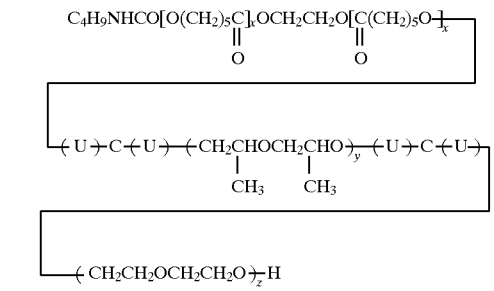

wherein an average molecular weight of poly ε-caprolactone is 530, an average molecular weight of PPG is 400, an average molecular weight of PEG is 1000, C represents —(CH$_2$)$_6$—, and (U) represents a urethane bond.

As is apparent from FIG. 1, the viscosity of Polymer A near its melting point is 7,200 centipoise, and Polymer A has a temperature dependency in such a manner that the viscosity decreases as the temperature increases. On the other hand, the viscosity of Polymer No. 1 of the present invention near its melting point is 2000 centipoise and the polymer has less temperature dependency. The viscosities of the both polymers become substantially equal at a temperature of 100° C. or more. The viscosity of 7200 centipoise is considered to be a relatively high value for dissolving and diffusing a drug, but it is considered that dissolution and diffusion are relatively easy if the viscosity at about 70° C. or more is less than 2000 centipoise. If Polymer A participates in the affinity to a relatively lipophilic drug and the amphipathicity of the polymer can function effectively, Polymer A can be a drug-storing layer having a preferred release control. On the other hand, Polymer No. 1 of the present invention has a viscosity of 2000 centipoise or less even at a low temperature and shows a low viscosity of 1000 centipoise or less at 55° C. or more. For this reason, Polymer No. 1 of the present invention has an advantage in that it is capable of dissolving a drug at a low temperature without using a solvent (when the drug is dissolved using a solvent, the solvent should be removed later by evaporation, and also an attention must be paid to the toxicity of a residual solvent and, further, it is difficult to completely remove the solvent having a high boiling point), and indicates that it is effective to drugs which are not resistant to heat. Furthermore, diffusion of the drug with Polymer No. 1 of the present invention is higher than that with Polymer A and there is a possibility that the drug is slowly released at a high releasing ratio only with a driving power by a concentration gradient. In addition, since the segment is hydrophilic, the polymer has a high water-sensitivity and absorbs moisture in an amount of several percents when it is allowed to stand in a room. The polymer has a property of that, upon heat-drying in vacuum, it can be dried to a moisture content of 0.3% or less and, therefore, it increases dissolution and diffusion of the drug by a very minute amount of moisture on the skin surface. This indicates that the polymer can be a storing layer and a release controlling layer effective to a hydrophilic drug. The above description is a fact well supporting the achievement of the object of the present invention.

(Solubility of Drugs)

Generally, many of drugs have their inherent melting points higher than ordinary temperatures. In other word, many of drugs are solid at ordinary temperatures. The drugs for transdermal absorption preparations which have been put into practical use until now also have such a tendency. Nitroglycerin and isosorbide dinitrate for angina pectoris are rare examples of liquid drugs, and are easily absorbed into a living body due to its strong permeability to skin or mucosa. For this reason, the drug having such a property can be easily formulated into a transdermal absorption preparation, though it is necessary to control the absorption by a release-controlling membrane. Rather, the majority of the drugs is solid at ordinary temperatures, relatively difficult to dissolve in solvents, and is less permeable into skin. However, in the case of the drug which takes effect with a small amount thereof, the drug may be transdermally absorbed in a small amount and, therefore, a base polymer for such drugs may have solubility at such a level. The base polymer according to the present invention has a solubility at such a level in a molten state, and generally, has an ability to dissolve the drug in the polymer on the order of from 1 to 100 mg, and, in specific examples, on the order of from 1 to 500 $\mu$g, at a drug concentration of from 0.1 to 6%. Some examples of the solubility are described hereinafter.

Each of anti-inflammatory agents, indomethacin (m.p.: 155°–162° C.), ketoprofen (m.p.: 94°–97° C.) and flurbiprofen (m.p.: 113°–116° C.) was dissolved in a molten base polymer No. 3 of Example, and each of the agents could be easily dissolved in an amount of more than 10 and several %. The SP value (Solubility Parameter: $cal^{0.5}cm^{-1.5}$) of each agent was 12.9, 11.6 and 12.0, which were found to relatively similar. The SP values of EO and PO are 9.4 and 8.7, respectively, and are far from the above values. However, it is considered that the urethane bond (18.5) and the terminal —OH (26.7) affect the easy dissolution of these drugs, and the non-affinity to the segment effectively acts on the release of the drugs. Also, glibenclamide (m.p.: 168°–173° C.) which is an anti-hyperglycemic agent and which is difficultly soluble could be dissolved in the base polymer No. 1 of the present invention in an amount of about 1%. Further, colchicine (m.p.: 176°–179° C.) which is especially effective to gout could be dissolved therein in an amount of several % or more. Also, Prostaglandin $E_1$ (m.p.: 119°–121° C.) which takes effect with a very small dose dissolved in the base polymers No. 1 to No. 6 in an amount of 2 to 3%.

(Safety and Stability)

Each of the alkylene oxides forming the segments of these base polymers is one of the materials having the highest purity among commercially available polymers and has been used as drugs and medical utility. The base polymer of the present invention is substantially free from skin irritation and thus applicable as plasters.

Further, each of the base polymers has a solidifying point similar to the skin temperature of the living body and, at a temperature below the skin temperature, it is a stable paste or a crystalline solid. Accordingly, stable storage of a drug for a long period of time is possible. Further, since there is no bleeding out of the drug as observed in a storing layer of a liquid, substantially no changes in the concentration of the drug was observed for a long period of time.

Industrial Applicability

As is apparent from the above descriptions, the base polymer for transdermal absorption preparation of the present invention is solid at ordinary temperatures and becomes liquid at a temperature near the skin temperature of human. In addition, the base polymer has a hydrophilic segment and heat-sensitive and water-sensitive characteristics. Also, the base polymer has a low viscosity in a molten state and has a property advantageous to the dissolution and diffusion of the drug. Accordingly, the base polymer of the present invention achieves a remarkable effect in that the drug which has not been easily formulated in a transdermal absorption preparation (i.e., the drug, etc. which is solid at ordinary temperatures, water-soluble and less absorbable into the skin, takes effect with a small amount, has a short half-life and is liable to be decomposed) can be stored stably for a long period of time and can be transdermally administered at a high releasing ratio and yet releasing slowly without irritation to the skin, and thus is a markedly practically useful base polymer.

What is claimed is:

1. A base polymer for a transdermal absorption preparation which comprises a heat-sensitive segmented polyurethane represented by the general formula:

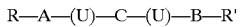

wherein A and B, which may be the same or different type of polymer or copolymer, each represents a polymer of ethylene oxide, propylene oxide, tetramethylane oxide or 1,2-butylene oxide, or a random or block copolymer thereof, with the proviso that A and B have different number average molecular weights when A and B are the same type of polymer or copolymer, wherein R and R', which may be the same or different, each represents a terminal H, $CH_3$, $C_2H_5$, $C_3H_7$, or $C_4H_9$ thereof, and wherein C represents a constituting structure which is a moiety of a diisocyanate compound excluding two isocyanate groups, (U) represents a urethane bond, at least one of A and B is hydrophilic and at the same time at least one of A and B is characterized in that it has a melting point near the temperature of human skin, and wherein the viscosity of the segmented polyurethane after melting is about 2,000 centipoise or less.

2. The base polymer for a transdermal absorption preparation as claimed in claim 1, wherein at least one of A and B is an ethylene oxide polymer.

3. The base polymer for a transdermal absorption preparation as claimed in claim 2, wherein a number average molecular weight of said ethylene oxide polymer is from 800 to 1,200.

4. The base polymer for a transdermal absorption preparation as claimed in claim 1, wherein at least one of R and R' is selected from the group consisting of $CH_3$, $C_2H_5$, $C_3H_7$ and $C_4H_9$.

5. The base polymer for a transdermal absorption preparation as claimed in claim 1, wherein a total molecular weight of said polymer is a number average molecular weight of from 1,000 to 6,000.

6. The base polymer for a transdermal absorption preparation as claimed in claim 1, wherein one of A and B is a polymer of ethylene oxide, propylene oxide, tetramethylene oxide or 1,2-butylene oxide, or a random or block copolymer thereof, and the other one of A and B is a random or block copolymer of ethylene oxide, propylene oxide, tetramethylene oxide, 1,2-butylene oxide or a combination thereof.

7. The base polymer for a transdermal absorption preparation as claimed in claim 1, wherein said diisocyanate compound is selected from the group consisting of p-phenylene diisocyanate, 2,4-toluylene diisocyanate (TDI), 4,4-diphenylmethane diisocyanate (MDI), naphthalene 1,5-diisocyanate, hexamethylene diisocyanate, tetramethylene diisocyanate, lysine diisocyanate, xylylene diisocyanate, hydrogenated TDI, hydrogenated MDI, dicyclohexyldimethylmethane p,p'-diisocyanate, and isophorone diisocyanate.

* * * * *